United States Patent
Florea

Patent Number: 6,099,532
Date of Patent: Aug. 8, 2000

[54] DISPOSABLE MONOMER DISPENSER AND VIAL BREAKER

[75] Inventor: Stefan I. Florea, North Arlington, N.J.

[73] Assignee: Howmedica Inc., New York, N.Y.

[21] Appl. No.: 09/114,592

[22] Filed: Jul. 13, 1998

[51] Int. Cl.⁷ ................................................. A61B 17/58
[52] U.S. Cl. ............................................. 606/93; 604/218
[58] Field of Search ........................ 606/92–93; 604/218; 225/97, 93

[56] References Cited

U.S. PATENT DOCUMENTS

| | | |
|---|---|---|
| 2,609,818 | 9/1952 | Parrine . |
| 3,040,743 | 6/1962 | Naess . |
| 3,506,606 | 4/1970 | Lange, Jr. . |
| 3,892,237 | 7/1975 | Steiner . |
| 4,277,184 | 7/1981 | Solomon .................................. 128/92 |
| 4,405,069 | 9/1983 | Vivier et al. .............................. 225/93 |
| 4,508,250 | 4/1985 | Punchak .................................... 225/97 |
| 4,546,767 | 10/1985 | Smith ....................................... 128/92 |
| 4,576,152 | 3/1986 | Muller at al. ............................. 128/92 |
| 4,751,921 | 6/1988 | Park ......................................... 128/92 |
| 4,779,763 | 10/1988 | Klawitter . |
| 5,219,897 | 6/1993 | Murray ..................................... 606/93 |
| 5,306,277 | 4/1994 | Bryant et al. ............................. 606/93 |
| 5,393,497 | 2/1995 | Haber et al. . |
| 5,514,137 | 5/1996 | Coutts ....................................... 606/93 |
| 5,558,136 | 9/1996 | Orrico ....................................... 606/93 |
| 5,681,317 | 10/1997 | Caldarise .................................. 606/93 |

FOREIGN PATENT DOCUMENTS 29 21 565  4/1980  Germany .

WO 97/07748  3/1997  WIPO .

*Primary Examiner*—Michael Buiz
*Assistant Examiner*—Jonathan D. Goldberg
*Attorney, Agent, or Firm*—Lerner, David, Littenberg, Krumholz & Mentlik, LLP

[57] ABSTRACT

A monomer dispenser and vial breaker includes a base portion and a cap portion which is attachable to the base portion. The base portion is substantially cylindrical, has an inner seat for supporting the shoulder of an ampoule, a knurled outer gripping surface, an exteriorly threaded portion, and an open end with a first locking structure. The cap portion is substantially cylindrical, has a first open end with interior threads and a second locking structure, a second open end, with a strainer and a vial breaking structure located between the first and second open ends. The cap portion is also provided with a knurled outer gripping surface. The monomer dispenser and vial breaker operate as follows: an ampoule is inserted into the base so that the shoulder of the ampoule rests on the inner seat, the cap is pushed onto the base so that locking structures engage, and the base and/or the cap are twisted relative to each other so that the threaded portions engage. As the cap and base are threaded together, the vial breaking structure breaks the bottom of the ampoule. The assembled device is then inverted to dispense the monomer through the second open end of the cap. After the dispenser is assembled and the monomer is dispensed, the locking structures prevent the device from being disassembled.

23 Claims, 5 Drawing Sheets

DISPOSABLE MONOMER DISPENSER AND VIAL BREAKER

BACKGROUND OF THE INVENTION

1. Field of the Invention

The invention relates to orthopaedic bone cement. More particularly, the invention relates to a vial breaker and dispenser for liquid monomer to be mixed with dry polymer as a cement component.

2. Brief Description of the Related Art

Orthopaedic bone cement generally consists of a dry polymer component and a liquid monomer component which must be mixed together thoroughly and quickly before the cement sets. The monomer component is usually packaged in a standard vial or ampoule which must be broken to release the monomer. The monomer must be dispensed quickly mixed with the polymer so that the cement may be properly prepared for use before it sets.

There are various known devices for facilitating the breaking of an ampoule and the dispensing of the ampoule contents. Many of these devices are not designed specifically for the dispensing of an orthopaedic cement monomer component. Furthermore, many of the devices are complex and utilize vacuum chambers and transfer vials or suction tubes.

U.S. Pat. No. 5,306,277 discloses a device which is specifically designed to break an ampoule and dispense a liquid monomer component of orthopaedic cement. The device generally includes a syringe adapted to receive an ampoule and adapted for connection to a vacuum source such that with the ampule open within the syringe body, the monomer is vacuumed out of the ampoule and into a mixing container.

Alternative embodiments accept an unbroken ampule and include an offset designed to break the ampule at its predetermined break point to permit the contents of the ampoule to be vacuumed from the ampule and transferred to the mixing container.

Although this type of device is relatively simple in construction, it has several disadvantages. It requires the use of a vacuum connection. The fluid exit port of the syringe is relatively narrow and constricts the flow of monomer. Glass fragments from the broken ampoule may also further constrict the flow of monomer out of the syringe. The relative size and configuration of the components are not ergonomically designed so that it is easy to drop the device during assembly.

Finally, there is no feature of the device which prevents if from being reused. The current preference with inexpensive medical devices is that they be made disposable rather than reusable since the expense of sterilizing a used device is more than the cost of a new device. Moreover, disposable devices are likely to fail is reused since their durability is premised on a single use.

SUMMARY OF THE INVENTION

It is therefore an object of the invention to provide a monomer dispenser which does not require a vacuum connection.

It is also an object of the invention to provide a monomer dispenser which has a wide exit port so that monomer may be quickly dispensed through the action of gravity.

It is another object of the invention to provide a monomer dispenser which will automatically break an ampoule and prevent glass fragments from interfering with the monomer flow.

It is still another object of the invention to provide a monomer dispenser/vial breaker which is ergonomically designed so that it is easy to use without the risk of dropping the device or risk of splashing monomer during utilization of the dispenser/vial breaker.

It is yet another object of the invention to provide a monomer dispenser/vial breaker which has a locking structure which prevents it from being used more than once.

In accord with these objects which will be discussed in detail below, the monomer dispenser and vial breaker of the invention include a base portion and a cap portion which is attachable to the base portion.

The base portion is substantially cylindrical, has an inner seat for supporting the shoulder of an ampoule, a knurled outer gripping surface, an exteriorly threaded portion, and an open end with a first locking structure.

The cap portion is substantially cylindrical, has a first open end with interior threads and a second locking structure, a second open end, with a strainer and a vial breaking structure (for example, without limitation, a pin structure) located between the first and second open ends. The cap portion is also provided with a knurled outer gripping surface.

According to a presently preferred embodiment, the first locking structure includes a plurality of resilient peripheral tapered barbs and the second locking structure includes an interior shelf dimensioned to allow the barbs to pass in one direction only.

The vial breaking structure is preferably located at the apex of a "tripod" structure, an example of which is a structure having an arched triple spoke design; and the tripod structure preferably carries the strainer which is preferably a stainless steel screen. According to the presently preferred embodiment, the vial breaking structure is a three faced off-axis pyramid.

Additional preferred features of the invention include interior ribs in the base which embrace an ampoule providing support so that it does not fall out of the base before the cap is attached and which allow for irradiation of the ampoule by, for example, exposure to gamma rays, for sterilization purposes; forming the second open end of the cap as a tapered exit port, and dimensioning the location of the locking structures and the threads such that the frangible bottom portion of an ampoule is located in a splash-free zone while the ampoule is being broken.

The monomer dispenser and vial breaker of the invention operates as follows: an ampoule containing the monomer is inserted into the base in an upside down position so that the should of the ampoule rests on the inner seat, the first open end of the cap is placed adjacent to the open end of the base, the cap is pushed onto the base so that the barbs pass the shelf, and the base and/or the cap are twisted relative to each other so that the threaded portions engage and bring the cap and base closer together.

As the cap and base are threaded together, the pyramidal vial breaking structure engages the bottom of the ampoule piercing (or otherwise breaking) it. The assembled device is then inverted to dispense the monomer through the second open end of the cap. The tripod structure of the device provides a strong support for the breaking structure as well as a large unobstructed path for the monomer to flow out of the dispenser.

After the dispenser is assembled and the monomer is dispensed, the locking structures prevent the device from being disassembled.

Additional objects and advantages of the invention will become apparent to those skilled in the art upon reference to the detailed description taken in conjunction with the provided figures.

DETAILED DESCRIPTION

Referring now to FIGS. 1–4, 4a, 5, 5a, 6, 7, and 7a, the monomer dispenser and vial breaker 10 of the invention includes a base portion 12 and a cap portion 14 which is attachable to the base portion 12.

Figure 1:
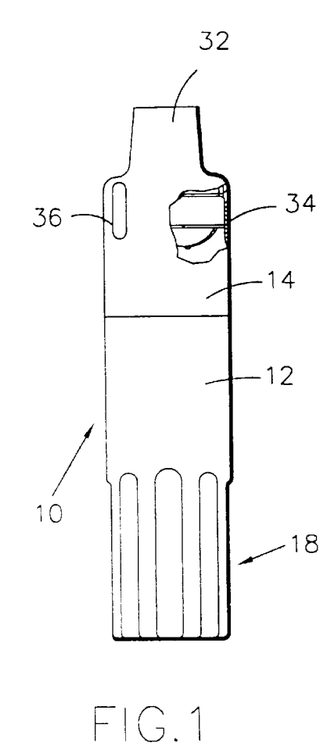
FIG. 1 is partially cut away side elevation view of the monomer dispenser and vial breaker of the invention.
Figure 2:
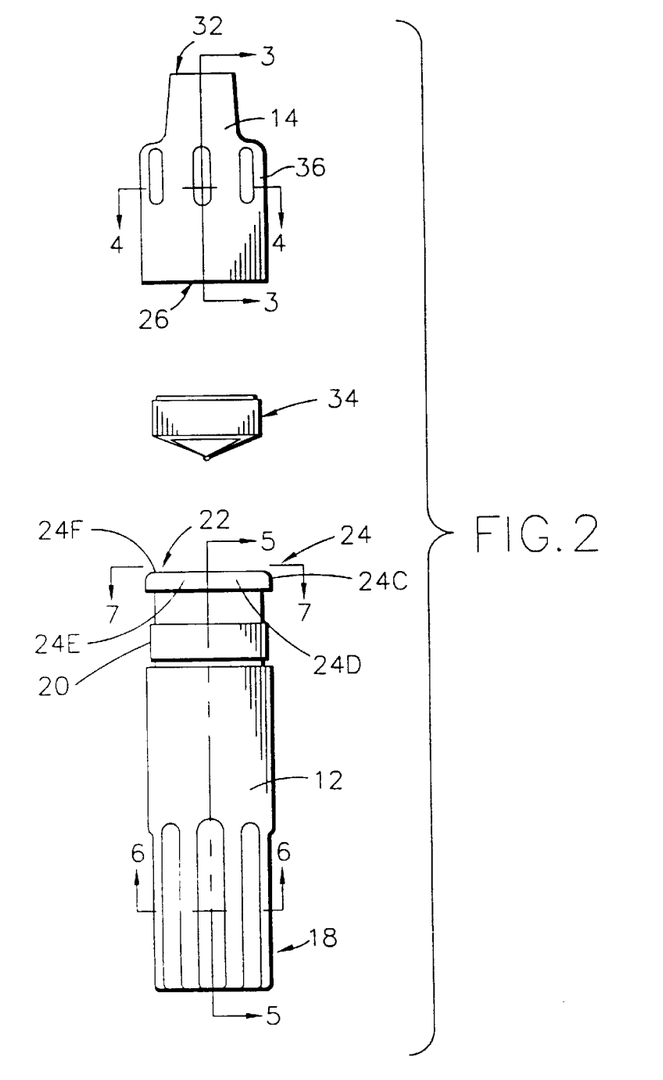
FIG. 2 is an exploded side elevation view of the invention.

The base portion 12 is substantially cylindrical, has an inner seat 16 for supporting the shoulder of an ampoule, a knurled outer gripping surface 18 (anti-slip flutes for efficient rotation and confident holding), an exteriorally threaded portion 20, and an open end 22 with a first locking structure 24.

According to a presently preferred embodiment, the threaded portion 20 is 1 1/16 by 20 thread. Those skilled in the art will readily appreciate that alternative threads may be utilized.

The cap portion 14 is substantially cylindrical, has a first open end 26 with interior threads 28 and a second locking structure 30, a second open end 32, with a strainer and a vial breaking structure 34 located between the first open end 26 and second open end 32.

The cap portion 14 is also provided with a knurled outer gripping surface 36.

As will be appreciated from FIGS. 2–4, the strainer and a vial breaking structure 34 may be removably coupled to the cap 14 as will be described in more detail hereinafter. Alternatively, the strainer and/or vial breaking structures may be fixed to the cap.

Figure 7:
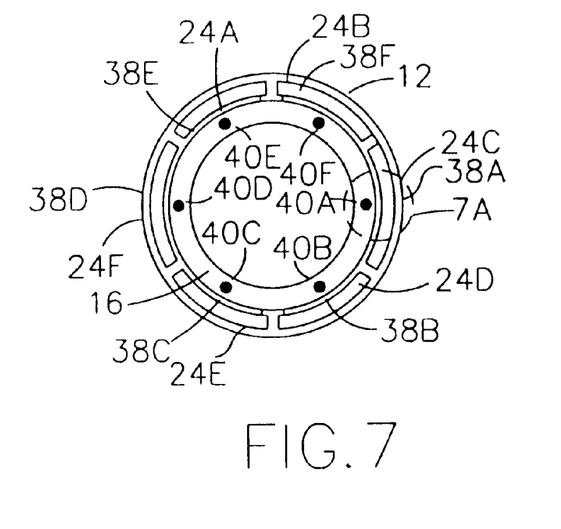
FIG. 7 is a view taken along line 7—7 in FIG. 2.

According to a presently preferred embodiment, the first locking structure 24 includes a plurality of resilient peripheral tapered barbs 24a–24f which are seen best in FIGS. 2 and 7. Accordingly, the second locking structure 30 is an interior shelf, seen best in FIG. 3, which is dimensioned to allow the barbs to pass in one direction only.

Figure 5:
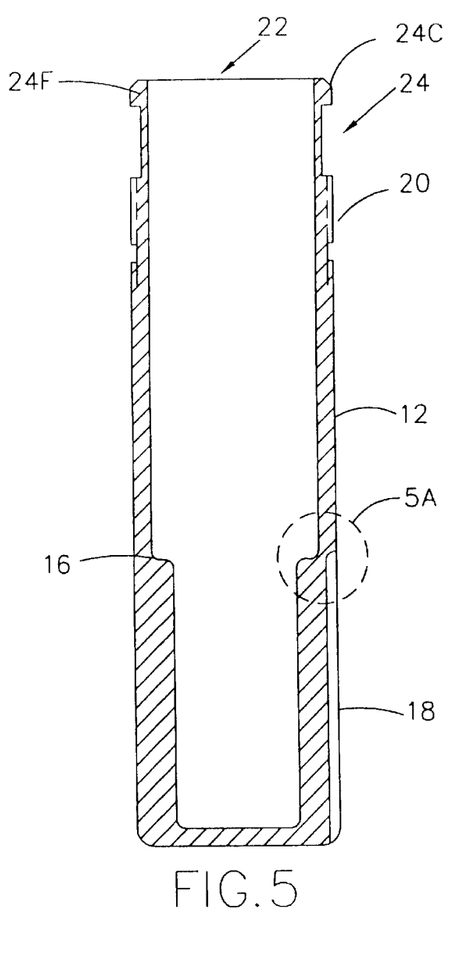
FIG. 5 is a sectional view taken along the line 5—5 in FIG. 2.
Figure 5A:
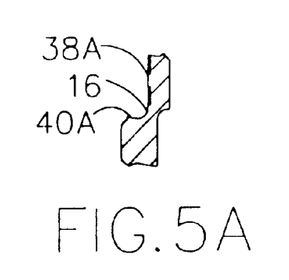
FIG. 5a is an enlarged detail of the portion 5a in FIG. 5.
Figure 6:
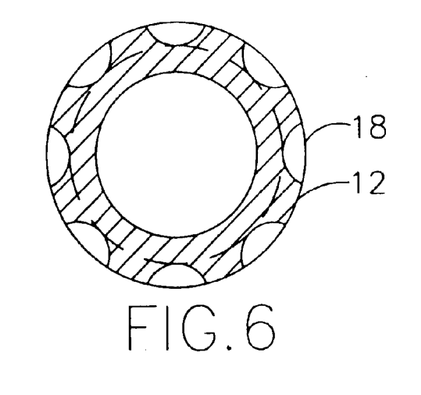
FIG. 6 is a sectional view taken along the line 6—6 in FIG. 2.
Figure 7A:
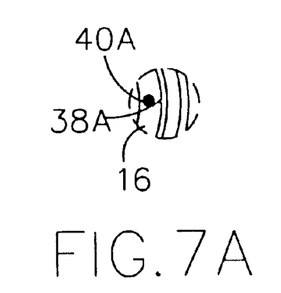
FIG. 7a is an enlarged detail of the portion 7a in FIG. 7.

The presently preferred base 12 includes a plurality of interior longitudinal ribs 38a–38f which are seen best in FIGS. 5a, 7, and 7a. These ribs are designed to embrace an ampoule so that it does not fall out of the base before the cap is attached and is designed with a thickness that allows for proper irradiation of the ampoule for sterilization purposes.

In addition, the inner seat 16 of the base 12 has a plurality of upstanding numbs 40a–40f which are also seen best in FIGS. 5a, 7, and 7a. These nubs engage the shoulder of the ampoule.

Figure 3:
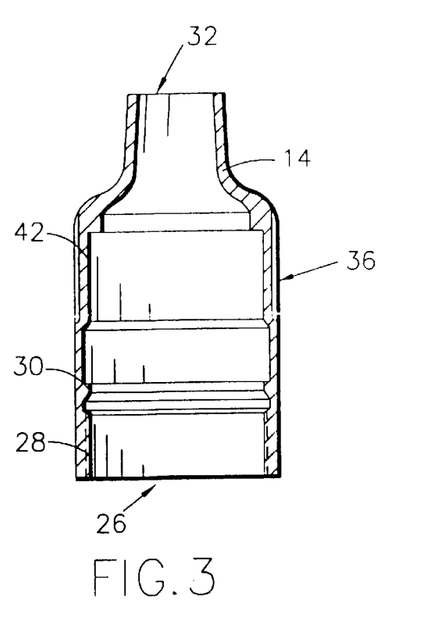
FIG. 3 is a sectional view taken along the line 3—3 in FIG. 2.
Figure 4:
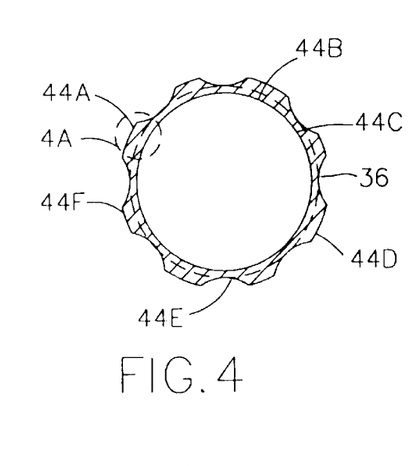
FIG. 4 is a sectional view taken along the line 4—4 in FIG. 2.
Figure 4A:
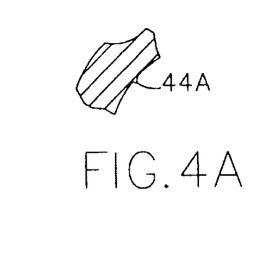
FIG. 4a is an enlarged detail of the portion 4a in FIG. 4.

As seen best in FIGS. 1, 3, and 4 the second open end 32 of the cap 14 is a tapered exit port and a non-tapered cylindrical wall 42 lies adjacent to the tapered end for receiving the strainer and vial breaking structure 34.

Accordingly, the cylindrical wall 42 is provided with a plurality of longitudinal surface ribs 44a–44f (seen best in FIGS. 4 and 4a) which are designed to embrace the strainer and vial breaking structure 34 and has a thickness which allows for proper irradiation of the ampoule for sterilization purposes, as explained hereinbefore.

Turning now to FIGS. 8–13, the strainer and vial breaking structure 34 has a generally cylindrical portion 46 and a depending tripod structure having three arms 48, 50, 52 which meet at a platform 54 which supports, according to an illustrative preferred embodiment of the invention, a depending pyramidal vial breaking structure 56. Alternative vial breaking structure shapes, i.e., vial breaking structures not necessarily having the aforementioned depending tripod structure, are all intended to come within the scope of the invention so long as they functionally are able to achieve the breaking of the ampoule when the cap and base are driven together as explained herein.

The illustrative tripod structure defines a generally conical space 58 within a strainer (for example, a stainless steel screen) 60 may be located. As seen best in FIGS. 10–13 the breaking structure 56, according to the illustrative embodiment of the invention, has a generally cylindrical portion 62 and a pyramidal tip 64. Pieces of glass that may result from the ampoule being broken can be prevented from being dispensed into the cement mix by stainer 60.

Figure 10:
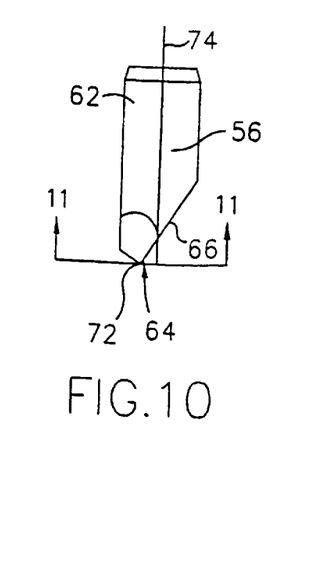
FIG. 10 is an enlarged side elevation view of the breaking structure of the invention.
Figure 11:
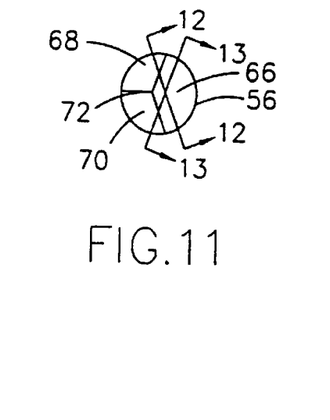
FIG. 11 is a view taken along line 11—11 in FIG. 10.
Figure 12:
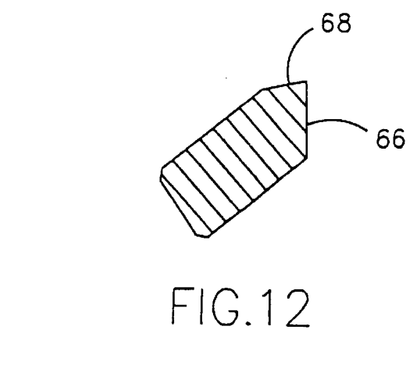
FIG. 12 is a sectional view taken along line 12—12 in FIG. 11.
Figure 13:
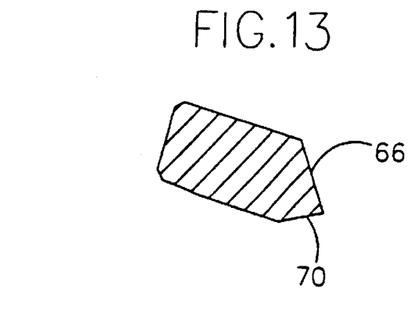
FIG. 13 is a sectional view taken along line 13—13 in FIG. 11.

The illustrative tip 64 of the breaking structure 56 has three planar faces 66, 68 and 70 which intersect at point 72 of the breaking structure. As shown in FIG. 10, in the preferred embodiment, point 72 is offset from centerline 74. Breaking structure 56 is designed to easily pierce or otherwise break the bottom of the ampoule to allow for the easy release of the fluid.

According to the presently preferred embodiment, all of the components of the invention, except for the stainless steel screen are made from injection molded plastic.

The overall size of an exemplary assembled device 10 (for practicing the invention using the exemplary device), as shown in FIG. 1 is approximately 5.39 inches by approximately 1.14 inches. The length of a corresponding illustrative mating cap 14 is approximately 2.12 inches and the diameter of an illustrative monomer exit port 32 is approximately 0.5 inches.

Figure 14A:
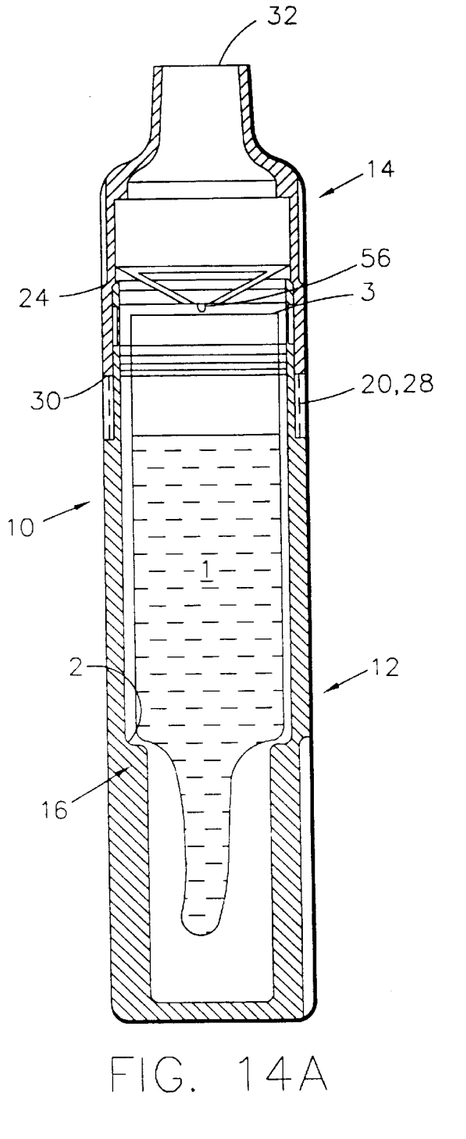
FIGS. 14A and 14B are cross sectional views of the invention assembled with an ampoule broken by the breaking structure.
Figure 14B:
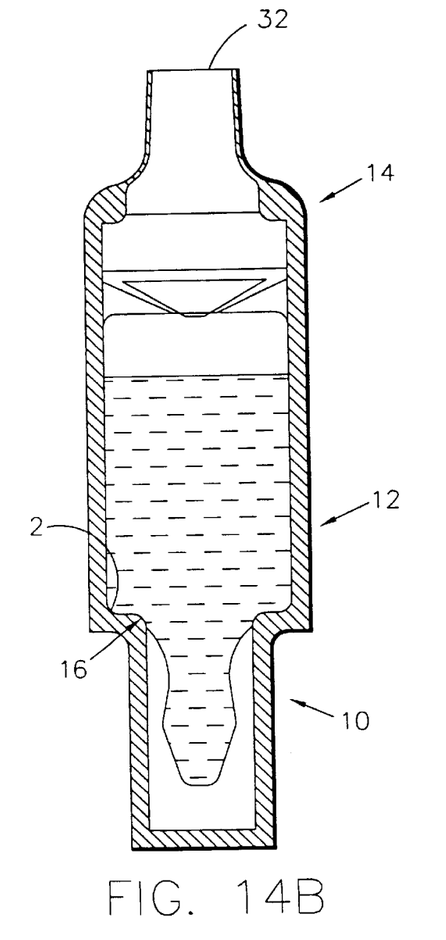

The overall length of the portion of a corresponding illustrative base 12 (which fits inside the cap 14) would be approximately 1 inch. The distance between the seat 16 and the open end of the base 12 is such that the shoulder of an ampoule is located within the wall of the base as shown in FIGS. 14A and 14B described below. This "protective wall" contains splashing when fluid is released from the ampoule.

Figure 8:
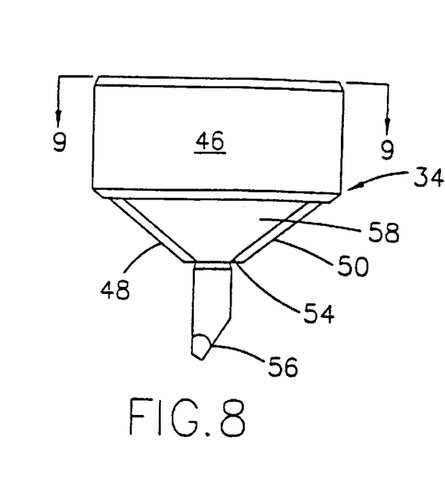
FIG. 8 is an enlarged side elevation view of the breaking structure and strainer assembly of the invention.
Figure 9:
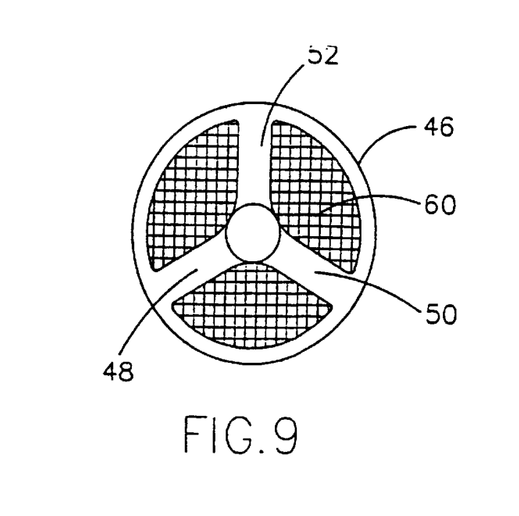
FIG. 9 is a view taken along line 9—9 in FIG. 8.

The overall diameter of the cylindrical portion 46 of illustrative strainer/breaker assembly 34 is approximately 0.97 inches; and the overall length of illustrative assembly 34 is approximately 0.71 inches.

As mentioned above, assembly 34 may be press fit into the cap 14 as seen in FIG. 1. The strainer 60 is preferably sonically welded to the arms 48, 50, 52, and the breaking structure 56 is preferably molded or press fit into the platform 54.

Turning now to FIGS. 14A and 14B, the monomer dispenser and vial breaker 10 of the invention operates as follows: an ampoule 1 containing the monomer is inserted in an upside down position into the base 12 so that the shoulder 2 of the ampoule rests on the inner seat 16, the first open end of the cap 14 is aligned adjacent to the open end of the base 12, the cap 14 is pushed onto the base 12 so that the barbs 24 pass the shelf 30, and the base and/or the cap are twisted relative to each other so that the threaded portions 20, 28 engage and bring the cap 14 and base 12 closer together.

As the cap 14 and base 12 are threaded together, the pyramidal vial breaking structure 56 is driven into position to engage the bottom 3 of the ampoule 1 until the ampoule breaks and the fluid is released. FIG. 14B shows ampoule 1 being broken by vial breaking structure 56.

The assembled device is then inverted to dispense the monomer through the second open end 32 of cap 14. In alternative embodiments of the invention a strainer like strainer 60 could be placed at the second open end 32 of cap 14.

The illustrative tripod structure of the device provides a strong support for the breaking structure 56 as well as a large unobstructed path for the monomer to flow out of the dispenser. Again, those of ordinary skill in the art will readily appreciate that alternative breaking structures are intended to come within the scope of the invention.

After the dispenser is assembled and the monomer is dispensed, the locking structures 24, 30 prevent the device from being disassembled.

There have been described and illustrated herein several embodiments of a monomer dispenser and vial breaker. While particular embodiments of the invention be limited thereto, as it is intended that the invention be have been described, it is not intended that the invention as broad in scope as the art will allow and that the specification be read likewise. Thus, while particular dimensions have been disclosed, it will be appreciated that some of the dimensions are dictated by the size of the vial and/or are set forth herein for the sake of illustrating the dimensions of devices suitable for implementing the teachings of the invention.

Also, while particular configurations have been shown with respect to the gripping surfaces, it will be recognized that other types of gripping surfaces could be used with similar results obtained.

Moreover, while particular configurations have been disclosed in reference to the locking structure, it will be appreciated that other configurations could be used as well.

Furthermore, while the strainer and vial breaking structure has been disclosed as having a tripod portion, it will be understood that a quadapod structure or pentapod structure can achieve the same or similar function as disclosed herein.

It will therefore be appreciated by those skilled in the art that yet other modifications could be made to the provided invention without deviating from its spirit and scope as so claimed.

What is claimed is:

1. A monomer dispenser and vial breaker comprising:
    a glass vial having a base;
    a substantially cylindrical body portion surrounding said vial having an open end with a first locking structure; and
    a cap portion mounted on the open end of said body and movable towards said vial and having a dispensing and an open end with a second locking structure and having a vial breaking structure for penetrating the base of said vial, said first locking structure being lockable to said second locking structure upon the penetration of said vial base by said vial breaking structure to prevent the reuse of the vial breaker.

2. A monomer dispenser and vial breaker according to claim 1 wherein said vial breaking structure includes a stem having a longitudinal axis and a planar surface forming an angle with said longitudinal axis.

3. A monomer dispenser and vial breaker according to claim 1 wherein said base portion has an inner seat for supporting the shoulder of the vial.

4. A monomer dispenser and vial breaker according to claim 3 wherein said base portion and said cap portion are dimensioned such that when an vial is placed in said base portion with said shoulder resting on said inner seat, the bottom of the vial will come in contact with said vial breaking structure when said cap portion and said base portion are locked together, causing said vial to break.

5. A monomer dispenser and vial breaker according to claim 1 wherein said base portion is ergonomically designed.

6. A monomer dispenser and vial breaker according to claim 1 wherein said base portion has a knurled outer gripping surface and said cap portion has a knurled outer gripping surface.

7. A monomer dispenser and vial breaker according to claim 1 wherein said base portion has a first threaded portion and said cap member has a second threaded portion which is engagable with said first threaded portion.

8. A monomer dispenser and vial breaker according to claim 1, wherein said cap portion has a strainer.

9. A monomer dispenser and vial breaker according to claim 8 wherein said strainer is substantially conical.

10. A monomer dispenser and vial breaker according to claim 1 wherein one of said first and second locking structures includes a plurality of resilient peripheral tapered barbs and the other locking structure includes an interior shelf dimensioned to allow the barbs to pass in one direction only.

11. A monomer dispenser and vial breaker according to claim 1 wherein said base portion includes a plurality of interior ribs for embracing vial.

12. A monomer dispenser and vial breaker according to claim 1 wherein said base portion includes a plurality of interior ribs dimensioned to allow the vial to be properly irradiated for sterilization purposes.

13. A monomer dispenser and vial breaker comprising:
    (a) a substantially cylindrical base member having an open end with a first threaded portion; and
    (b) a cap member having an open dispensing end, an open end with a second threaded portion, and a vial breaking structure, said second threaded portion being engagable with said first threaded portion, wherein said vial breaking structure includes a stem having a longitudinal axis and a planar surface forming an angle with said longitudinal axis.

14. A monomer dispenser and vial breaker according to claim 13 wherein said vial breaking structure includes a stem having a longitudinal axis and three planar surfaces each forming an angle with said longitudinal axis.

15. A monomer dispenser and vial breaker according to claim 13 wherein said cap member includes a substantially conical structure and said breaking structure is located at the apex of said conical structure.

16. A monomer dispenser and vial breaker according to claim 15 wherein said substantially conical structure is a tripod structure.

17. A monomer dispenser and vial breaker according to claim 16 wherein said substantially conical structure contains a strainer.

18. A method for opening an ampoule and dispensing a liquid contained in the ampoule utilizing a vial breaker having (a) a substantially cylindrical base portion with an open end, said base portion including a first locking structure, an inner seat for supporting the shoulder of the ampoule and a first threaded portion; and (b) a cap portion having an open dispensing end, an open end with a second locking structure being lockable to said first locking structure such that said monomer dispenser and vial breaker cannot be reused and a vial breaking structure, and a second threaded portion which is engagable with said first threaded portion, comprising the steps of:

(a) inserting the ampoule into said base so that the shoulder of said ampoule rests on said inner seat, (b) pushing said cap onto said base so that said first locking structure and said second locking structure engage one another; and (c) twisting said base and/or said cap relative to one another so that said first threaded portion and said second threaded portion engage one another and drive said vial breaking structure as said base and/or cap are twisted so that said vial breaking structure breaks through the bottom of the ampoule.

19. A method as set forth in claim 18 further comprising the step of inverting said vial breaker to dispense the monomer through the second open end of said cap.

20. A method as set forth in claim 19 further comprising the step of straining said liquid to prevent broken portions of said ampoule from being dispensed.

21. A method as set forth in claim 20 wherein said step of pushing said cap onto said base so that said first locking structure and said second locking structure engage one another, prevents said cap and said base from being separated to thereby prevent reuse of said vial breaker.

22. A monomer dispenser and vial breaker, comprising:

(a) a substantially cylindrical base portion having an open end with a first locking structure; and (b) a cap portion having an open dispensing end, an open end with a second locking structure, and a vial breaking structure, said second locking structure being lockable to said first locking structure, such that said monomer dispenser and vial breaker cannot be reused, wherein said vial breaking structure includes a stem having a longitudinal axis and a planar surface forming an angle with said longitudinal axis.

23. A monomer dispenser and vial breaker, comprising:

(a) a substantially cylindrical base portion having an open end with a first locking structure; and (b) a cap portion having an open dispensing end, an open end with a second locking structure, and a vial breaking structure, said second locking structure being lockable to said first locking structure, such that said monomer dispenser and vial breaker cannot be reused, wherein one of said first and second locking structures includes a plurality of resilient peripheral tapered barbs and the other locking structure includes an interior shelf dimensioned to allow the barbs to pass in one direction only.

\* \* \* \* \*

UNITED STATES PATENT AND TRADEMARK OFFICE
CERTIFICATE OF CORRECTION

| | | |
|---|---|---|
| PATENT NO. | : | 6,099,532 |
| DATED | : | August 8, 2000 |
| INVENTOR(S) | : | Florea |

It is certified that error appears in the above-identified patent and that said Letters Patent is hereby corrected as shown below:

Column 2, line 50, "should" should read -- shoulder --.
Column 4, line 41, after "within" insert -- which --.
Column 5, line 47, cancel the words "be imited".
Column 5, line 48, cancel the words "thereto, as it is intended that the invention be".
Column 5, line 49, after "invention" insert -- be --.
Column 6, line 12, after "dispensing" insert -- end --.
Column 6, line 28, "an" should read -- a --.

Signed and Sealed this

Seventeenth Day of April, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO. : 6,099,532
DATED : August 8, 2000
INVENTOR(S) : Stefan I. Florea

It is certified that error appears in the above-identified patent and that said Letters Patent is hereby corrected as shown below:

<u>Title page,</u>
Item [73], Assignees, should read -- Stryker Technologies Corporation, Kalamazoo, Mich. --

Signed and Sealed this

Tenth Day of May, 2005

JON W. DUDAS
*Director of the United States Patent and Trademark Office*